United States Patent
Li et al.

(10) Patent No.: US 10,809,339 B2
(45) Date of Patent: Oct. 20, 2020

(54) SYSTEM AND METHOD FOR PERFORMING MAGNETIC RESONANCE DIFFUSION WEIGHTED IMAGING OF AN OBJECT

(71) Applicant: GE Precision Healthcare LLC, Wauwatosa, WI (US)

(72) Inventors: Ke Li, Pewaukee, WI (US); Gaohong Wu, New Berlin, WI (US); Eric Printz, Oconomowoc, WI (US); Kenichi Kanda, Brookfield, WI (US); Margaret Ann Wiza, New Berlin, WI (US)

(73) Assignee: GE PRECISION HEALTHCARE LLC, Wauwatosa, WI (US)

(*) Notice: Subject to any disclaimer, the term of this patent is extended or adjusted under 35 U.S.C. 154(b) by 214 days.

(21) Appl. No.: 15/927,218

(22) Filed: Mar. 21, 2018

(65) Prior Publication Data

US 2018/0284211 A1 Oct. 4, 2018

Related U.S. Application Data (60) Provisional application No. 62/476,038, filed on Mar. 24, 2017.

(51) Int. Cl.
| | |
|---|---|
| *G01R 33/56* | (2006.01) |
| *G01R 33/563* | (2006.01) |
| *A61B 5/055* | (2006.01) |
| *G01R 33/54* | (2006.01) |
| *G01R 33/483* | (2006.01) |

(52) U.S. Cl.
CPC ........ *G01R 33/56341* (2013.01); *A61B 5/055* (2013.01); *G01R 33/543* (2013.01); *G01R 33/4835* (2013.01)

(58) Field of Classification Search
CPC .... G01R 33/543; G01R 33/4835; A61B 5/055
See application file for complete search history.

(56) References Cited

U.S. PATENT DOCUMENTS

| | | | |
|---|---|---|---|
| 6,323,646 B1 | 11/2001 | Zhou et al. | |
| 2009/0208422 A1* | 8/2009 | Mardor ................ | A61K 31/337 424/9.364 |
| 2011/0254548 A1* | 10/2011 | Setsompop ........ | G01R 33/4835 324/309 |
| 2012/0049845 A1* | 3/2012 | Bito ..................... | G01R 33/485 324/309 |
| 2012/0226138 A1* | 9/2012 | DeSalles ................ | G01R 33/56 600/411 |
| 2013/0335080 A1* | 12/2013 | Jo ....................... | G01R 33/4824 324/309 |
| 2014/0091790 A1* | 4/2014 | Huwer ................... | G01R 33/56 324/307 |
| 2015/0108976 A1* | 4/2015 | Fischer .............. | G01R 33/5616 324/309 |
| 2017/0072016 A1* | 3/2017 | Gallo ................... | A61M 11/007 |

(Continued)

*Primary Examiner* — Alvaro E Fortich (74) *Attorney, Agent, or Firm* — Armstrong Teasdale LLP (57) ABSTRACT

Methods and systems for performing magnetic resonance diffusion weighted imaging of an object is provided. The method includes applying a plurality of diffusion gradients to a plurality of image slices of the object during a plurality of repetition times via an MRI system. A different diffusion gradient of the plurality is applied to each image slice during the same repetition time.

20 Claims, 4 Drawing Sheets

| TR | 110 | Slice 1 | 2 | 3 | 4 | 5 | 6 | 7 |
|---|---|---|---|---|---|---|---|---|
| 1 | T2 | → | | | | | | |
| 2 | B 1000 | X | Y | Z | X | Y | Z | X |
| 3 | B 1000 | Y | Z | X | Y | Z | X | Y |
| 4 | B 1000 | Z | X | Y | Z | X | Y | Z |

96

(56) References Cited

U.S. PATENT DOCUMENTS

2017/0146631 A1* 5/2017 Beck ................. G01R 33/5608
2017/0234956 A1* 8/2017 Feiweier .......... G01R 33/56341
                                                            324/309

* cited by examiner

| TR | 110 | Slice 1 | 2 | 3 | 4 | 5 | 6 | 7 |
|---|---|---|---|---|---|---|---|---|
| 1 | T2 | → | | | | | | |
| 2 | B 1000 | X | Y | Z | X | Y | Z | X |
| 3 | B 1000 | Y | Z | X | Y | Z | X | Y |
| 4 | B 1000 | Z | X | Y | Z | X | Y | Z |

SYSTEM AND METHOD FOR PERFORMING MAGNETIC RESONANCE DIFFUSION WEIGHTED IMAGING OF AN OBJECT

CROSS REFERENCE

The present application claims benefit of U.S. Provisional Application Ser. No. 62/476,038 filed Mar. 24, 2017, which is incorporated herein by reference in its entirety.

TECHNICAL FIELD

Embodiments of the invention relate generally to magnetic resonance imaging ("MRI") systems, and more specifically, to a system and method for performing magnetic resonance diffusion weighted imaging of an object.

BACKGROUND

MRI is a widely accepted and commercially available technique for obtaining digitized visual images representing the internal structure of objects having substantial populations of atomic nuclei that are susceptible to nuclear magnetic resonance ("NMR"). Many MRI systems use superconductive magnets to scan a subject/patient via imposing a strong main magnetic field on the nuclei in the subject to be imaged. The nuclei are excited by a radio frequency ("RF") signal/pulse transmitted by a RF coil at characteristics NMR (Larmor) frequencies. By spatially disturbing localized magnetic fields surrounding the subject and analyzing the resulting RF responses from the nuclei as the excited protons relax back to their lower energy normal state, a map or image of these nuclei responses as a function of their spatial location is generated and displayed. An image of the nuclei responses provides a non-invasive view of a subject's internal structure.

Magnetic resonance diffusion weighted imaging ("DWI") is a form of MRI that uses the diffusion of molecules of a material, e.g., water, to generate contrast in MR images. In particular, DWI utilizes gradient coils to generate diffusion gradients at the beginning of a pulse sequence to sensitize the acquired NMR signals to the movements of the molecules, whereby stationary molecules give a stronger MR signal than moving molecules. As the difference in signal strength between molecules corresponds to the amount of movement of the molecules, an image and/or map of measurable diffusion rates of the molecules within the object can be generated.

Many DWI methods map/measure diffusion of molecules in two or more directions, e.g., along the x, y, and z axes of the object, by applying diffusion gradients in the same directions. Accordingly, many such DWI methods typically apply the diffusion gradients one at a time during sequenced repetition times, known as "TRs", to a series of image slices of the object. For example, many such DWI methods will first apply an x-axis oriented diffusion gradient to all of the image slices during a first TR, then apply a y-axis oriented diffusion gradient to all of the image slices during a second TR, and then finally apply a z-axis oriented diffusion gradient to all of the image slices during a third TR. Such diffusion gradient sequencing, however, usually involves repeated use of the same diffusion gradient over a short period of time, which in turn often results in the generation of stressors, e.g., high amounts of heat, within the gradient coils.

What is needed, therefore, is an improved system and method for performing DWI of an object.

SUMMARY

In an embodiment, a method for performing magnetic resonance diffusion weighted imaging of an object is provided. The method includes applying a plurality of diffusion gradients to a plurality of image slices of the object during a plurality of repetition times via an MRI system. A different diffusion gradient of the plurality is applied to each image slice during the same repetition time.

In another embodiment, an MRI system for performing magnetic resonance diffusion weighted imaging of an object is provided. The MRI system includes an MRI controller in electronic communication with a magnet assembly. The MRI controller is operative to apply a plurality of diffusion gradients to a plurality of image slices of the object during a plurality of repetition times via the magnet assembly. A different diffusion gradient of the plurality is applied to each image slice during the same repetition time.

In yet another embodiment, a non-transitory computer readable medium storing instructions is provided. The stored instructions are configured to adapt an MRI controller to apply a plurality of diffusion gradients to a plurality of image slices of an object during a plurality of repetition times via a magnet assembly. A different diffusion gradient of the plurality is applied to each image slice during the same repetition time.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. As used herein the terms "optical communication", "optically communicate" and "optically connected" mean that the referenced elements are able to direct, reflect, and/or receive photons between each other. The term "diffusion gradient," as used herein, refers to a magnetic gradient generated/applied by one or more gradient coils of an MRI system and oriented along a direction for the purpose of facilitating DWI. Accordingly, the terms "differing diffusion gradients" and "different diffusion gradients," as used herein, refer to diffusion gradients oriented along different directions and/or having other characteristics distinguishing themselves from each other. The terms "rest," "rested," and "resting," as used herein with respect to a gradient coil, refers to a time period during which the gradient coil is not energized, or energized to a lesser extent than it would be if it were the primary contributor to a generated diffusion gradient.

Further, while the embodiments disclosed herein are described with respect to an MRI system, it is to be understood that embodiments of the present invention may be applicable to other imaging systems which generate magnetic gradients. Further still, as will be appreciated, embodiments of the present invention related imaging systems may be used to analyze tissue generally and are not limited to human tissue.

Figure 1:
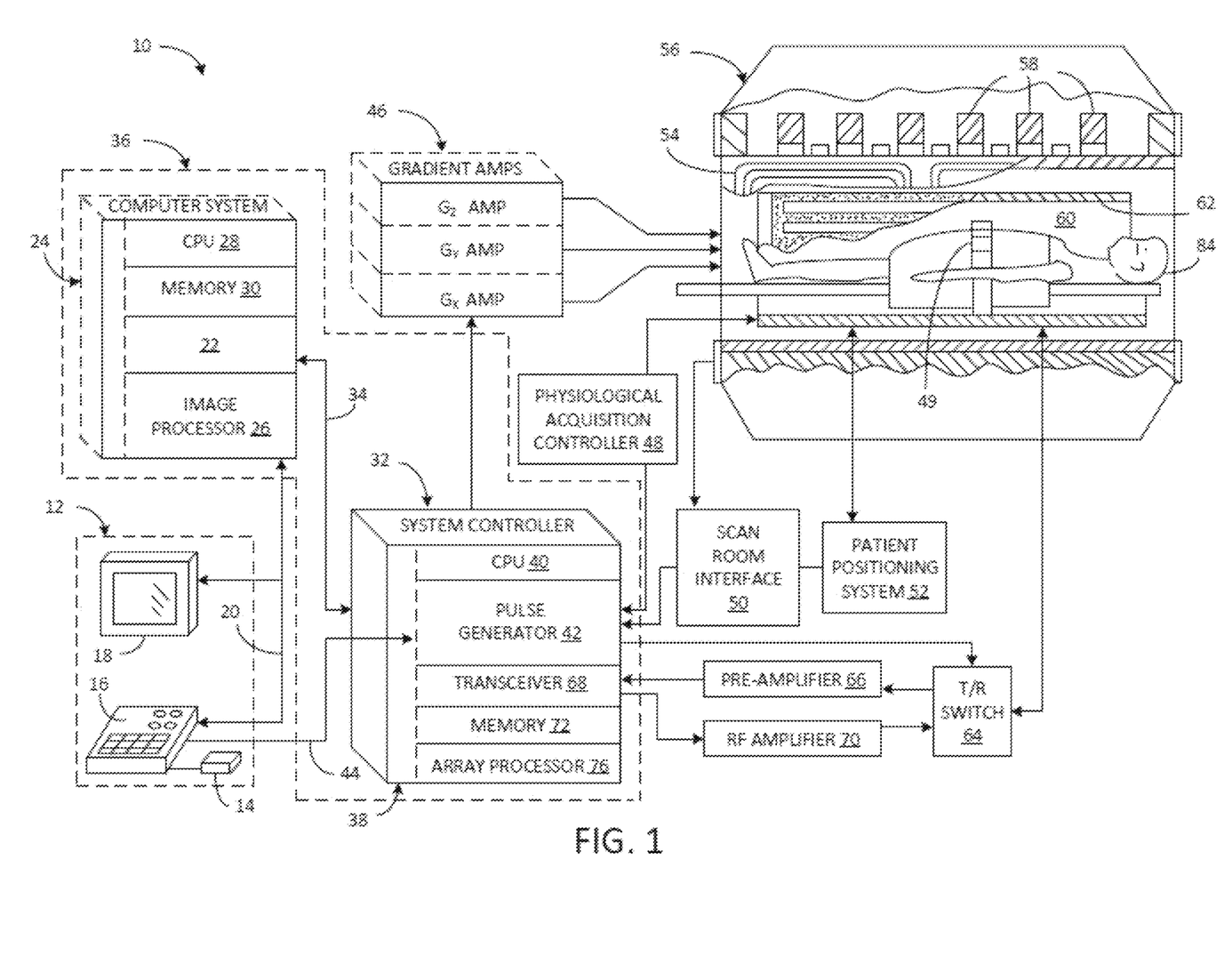
FIG. 1 is a block diagram of an exemplary MRI system, in accordance with an embodiment of the present invention.

Referring now to FIG. 1, the major components of an MRI system 10 incorporating an embodiment of the invention are shown. Operation of the system 10 is controlled from the operator console 12, which includes a keyboard or other input device 14, a control panel 16, and a display screen 18. The console 12 communicates through a link 20 with a separate computer system 22 that enables an operator to control the production and display of images on the display screen 18. The computer system 22 includes a number of modules, which communicate with each other through a backplane 24. These include an image processor module 26, a CPU module 28 and a memory module 30, which may include a frame buffer for storing image data arrays. The computer system 22 communicates with a separate system control or control unit 32 through a high-speed serial link 34. The input device 14 can include a mouse, joystick, keyboard, track ball, touch activated screen, light wand, voice control, or any similar or equivalent input device, and may be used for interactive geometry prescription. The computer system 22 and the MRI system control 32 collectively form an "MRI controller" 36.

The MRI system control 32 includes a set of modules connected together by a backplane 38. These include a CPU module 40 and a pulse generator module 42, which connects to the operator console 12 through a serial link 44. It is through link 44 that the system control 32 receives commands from the operator to indicate the scan sequence that is to be performed. The pulse generator module 42 operates the system components to execute the desired scan sequence and produces data which indicates the timing, strength and shape of the RF pulses produced, and the timing and length of the data acquisition window. The pulse generator module 42 connects to a set of gradient amplifiers 46, to indicate the timing and shape of the gradient pulses that are produced during the scan. The pulse generator module 42 can also receive patient data from a physiological acquisition controller 48 that receives signals from a number of different sensors connected to the patient, such as ECG signals from electrodes attached to the patient. And finally, the pulse generator module 42 connects to a scan room interface circuit 50, which receives signals from various sensors associated with the condition of the patient and the magnet system. It is also through the scan room interface circuit 50 that a patient positioning system 52 receives commands to move the patient to the desired position for the scan.

The pulse generator module 42 operates the gradient amplifiers 46 to achieve desired timing and shape of the gradient pulses that are produced during the scan. The gradient waveforms produced by the pulse generator module 42 are applied to the gradient amplifier system 46 having Gx, Gy, and Gz amplifiers. Each gradient amplifier excites a corresponding physical gradient coil in a gradient coil assembly, generally designated 54, to produce the magnetic field gradients used for spatially encoding acquired signals. The gradient coil assembly 54 forms part of a magnet assembly 56, which also includes a polarizing magnet 58 (which in operation, provides a homogenous longitudinal magnetic field $B_0$ throughout a target volume 60 that is enclosed by the magnet assembly 56) and a whole-body (transmit and receive) RF coil 62 (which, in operation, provides a transverse magnetic field $B_1$ that is generally perpendicular to $B_0$ throughout the target volume 60). In some embodiments, an RF surface coil 49 is used for imaging different anatomies of a patient 84 undergoing a MRI scan. The body coil 62 and surface coils 49 may be configured to operate in a transmit and receive mode, transmit mode, or receive mode.

The resulting signals emitted by the excited nuclei in the patient may be sensed by the body coil 62 and/or surface coil 49 and coupled through the transmit/receive switch 64 to a preamplifier 66. The amplifier MR signals are demodulated, filtered, and digitized in the receiver section of a transceiver 68. The transmit/receive switch 64 is controlled by a signal from the pulse generator module 42 to electrically connect an RF amplifier 70 to the body coil 62 and/or surface coil 49 during the transmit mode and to connect the preamplifier 66 to the body coil 62 and/or surface coil 49 during the receive mode.

The MR signals picked up by the RF coil 62 are digitized by the transceiver module 68 and transferred to a memory module 72 in the system controller 32. A scan is complete when an array of raw k-space data has been acquired in the memory module 72. This raw k-space data/datum is rearranged into separate k-space data arrays for each image to be reconstructed, and each of these is input to an array processor 76 which operates to Fourier transform the data into an array of image data. This image data is conveyed through the serial link 34 to the computer system 22 where it is stored in memory 30. In response to commands received from the operator console 12, this image data may be archived in long-term storage or it may be further processed by the image processor 26 and conveyed to the operator console 12 and presented on the display 18.

Figure 2:
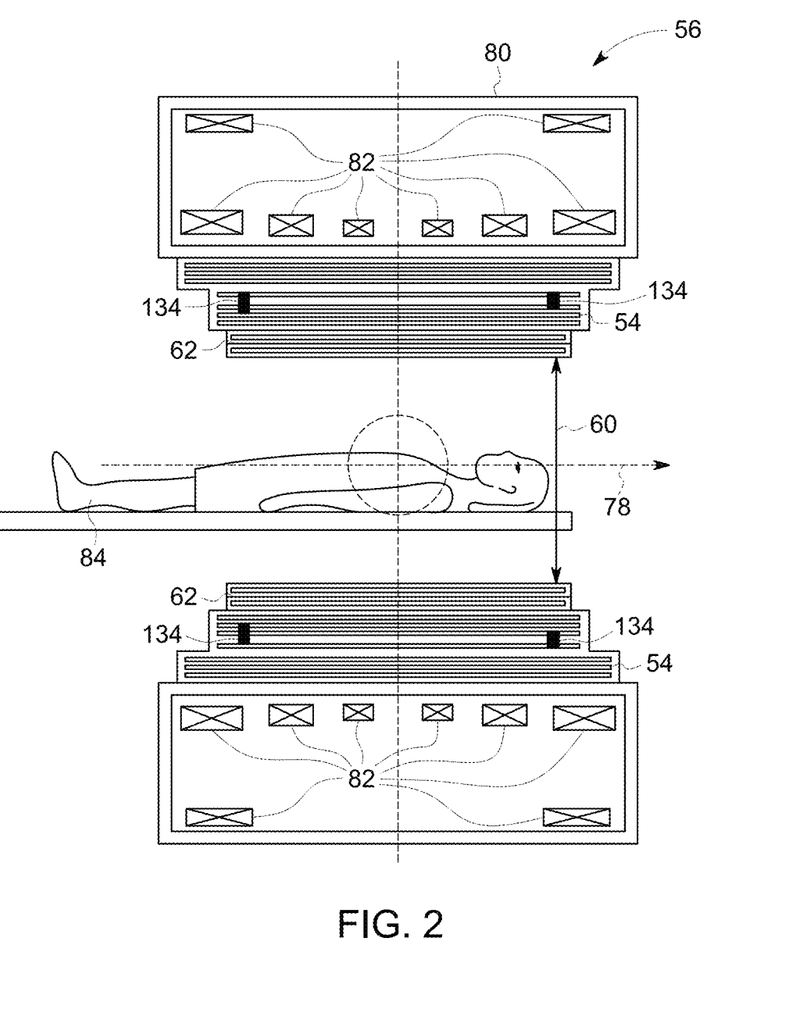
FIG. 2 is a schematic cross-sectional view of a magnet assembly of the MRI system of FIG. 1, in accordance with an embodiment of the present invention.

As illustrated in FIG. 2, a schematic side elevation view of the magnet assembly 56 is shown in accordance with an embodiment of the invention. The magnet assembly 56 is cylindrical in shape having a center axis 78. The magnet assembly 56 includes a cryostat 80 and one or more radially aligned longitudinally spaced apart superconductive coils 82 that form the polarizing magnet 58. The superconductive coils 82 are capable of carrying large electrical currents and are designed to create the $B_0$ field within the patient/target volume 60. As will be appreciated, the magnet assembly 56 may further include both a terminal shield and a vacuum vessel (not shown) surrounding the cryostat 80 in order to help insulate the cryostat 80 from heat generated by the rest of the MRI system 10 (FIG. 1). The magnet assembly 56 may still further include other elements such as covers, supports, suspension members, end caps, brackets, etc. (not shown). While the embodiment of the magnet assembly 56 shown in FIGS. 1 and 2 utilizes a cylindrical topology, it should be understood that topologies other than cylindrical may be used. For example, a flat geometry in a split-open MRI system may also utilize embodiments of the invention described below. As further shown in FIG. 2, a patient/object/imaged subject 84 is inserted into the magnet assembly 56.

Turning now to FIGS. 3-6, the gradient coil assembly 54 is shown in conjunction with various gradient coils 86, 88, and 90 of the gradient coil assembly 54. As will be understood, in embodiments, the gradient coil assembly 54 may include an x-gradient coil 86 (best seen in FIG. 4) operative to generate/apply a diffusion gradient along/corresponding to an x-axis 92, a y-gradient coil 88 (best seen in FIG. 5) operative to generate/apply a diffusion gradient along/corresponding to a y-axis 94, and a z-gradient coil 90 (best seen in FIG. 6) operative to generate/apply a diffusion gradient along/corresponding to a z-axis 78, which may be the same as the central axis 78 of the magnet assembly 56. As will be appreciated, in addition to applying diffusion gradients oriented along the axes 78, 92, and 94, the gradient coils 86, 88, and 90 may be utilized to apply diffusion gradient gradients along/corresponding to any direction within the space defined by the three axes 78, 92, and 94.

Moving now to FIGS. 7-10, a diagram of a diffusion gradient sequence 96 (FIG. 7) and corresponding pulse sequences 98 (FIG. 8), 100 (FIG. 9), and 102 (FIG. 10) for different diffusion gradients applied in conformance with the diffusion gradient sequence 96, according to an embodiment of the present invention, are shown. As will be understood, the MRI controller 36 is operative to apply a plurality of diffusion gradients (represented by the boxes marked x, y, and z in FIG. 7) to a plurality of image slices (represented by the vertical columns marked Slices 1-7 in FIG. 7) during a plurality of repetition times (represented by the horizontal rows marked TR 1-4 in FIG. 7) via the magnet assembly 56. As will be further understood, diffusion gradients marked x, y, and z within the diffusion gradient sequence 96 correspond to diffusion gradients generated by the gradient coils 86, 88, 90, and applied to the object 84 in directions corresponding to the x, y, and z axes, respectively.

Figure 7:
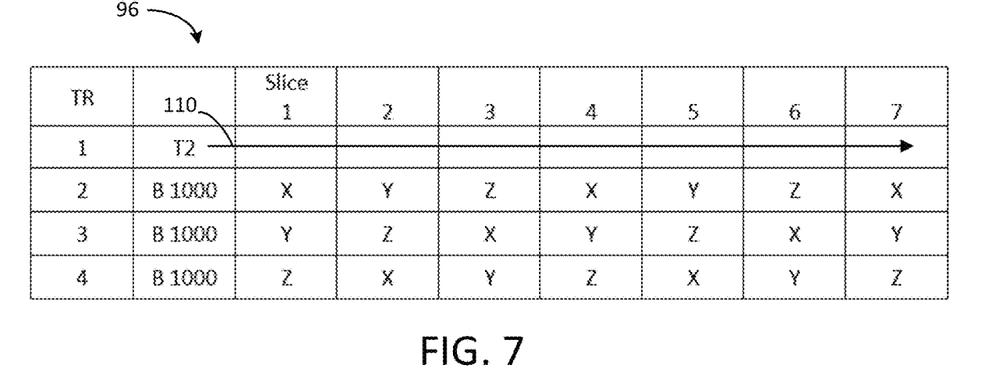
FIG. 7 is a table showing a diffusion gradient sequence, in accordance with an embodiment of the present invention.
Figure 8:
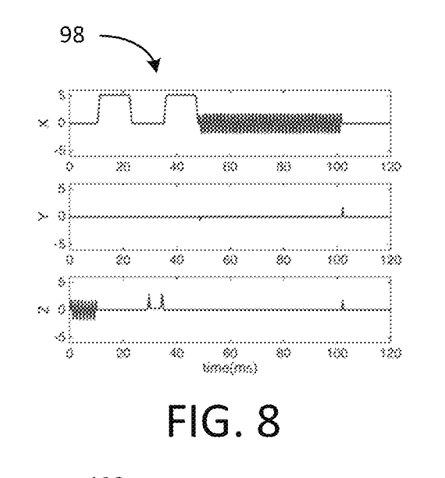
FIG. 8 is a diagram of a pulse sequence for applying a diffusion gradient for slice 1 of TR2 of FIG. 7.
Figure 9:
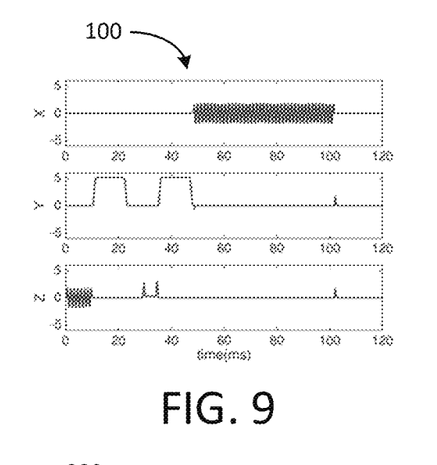
FIG. 9 is a diagram of a pulse sequence for applying a diffusion gradient for slice 2 of TR2 of FIG. 7.
Figure 10:
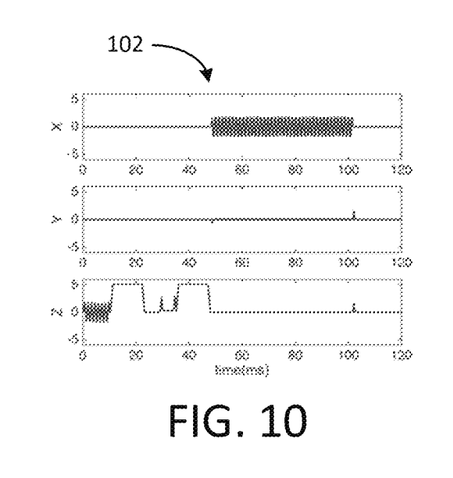
FIG. 10 is a diagram of a pulse sequence for applying a diffusion gradient for slice 3 of TR2 of FIG. 7.

As shown by the diffusion gradient sequence 96, a different diffusion gradient of the plurality is applied to each image slice 106 during the same repetition time TR. For example, as further shown by the diffusion gradient sequence 96, in embodiments, the MRI controller 36 may first apply an x-diffusion gradient to the first image slice, hereafter also referred to as "Slice 1", then apply a y-diffusion gradient to a second image slice, hereafter also referred to as "Slice 2, and then apply a z-diffusion gradient to a third image slice, hereafter also referred to as "Slice 3", all within the same TR (TR 2). During the next TR (TR 3), the MRI controller 36 may then apply a y-diffusion gradient to Slice 1, then a z-diffusion gradient to Slice 2, and then an x-diffusion gradient to Slice 3. As indicated by additional Slices 4-7, the number of slices 106 within the diffusion gradient sequence 96 may vary based on the specifications of the MRI system 10 and/or the size of the object 84. In other words, embodiments of the invention may utilize as many or as few slices necessary to image the object 84.

Figure 6:
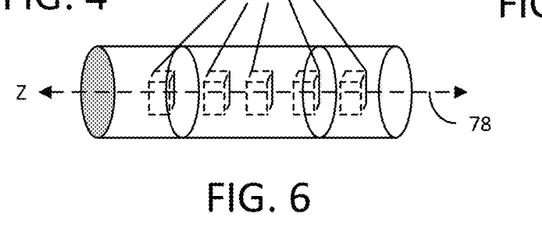
FIG. 6 is a diagram of a z-axis gradient coil of the gradient coil assembly of FIG. 3, in accordance with an embodiment of the present invention.

Briefly referring back to FIG. 6, in embodiments, the slices 106 may be oriented along the same axis. For example, as shown in FIG. 6, the slices 106 may be oriented along the z-axis 78 which, in embodiments, may also be the longitudinal axis of the object 84. The slices 106 may also be arranged in sequential order such that Slice 1 is adjacent to Slice 2, which is in turn adjacent to Slice 3, which is in turn adjacent to Slice 4, etc. Additionally, while the slices 106 are depicted in FIG. 6 as being spaced apart, it will be understood that, in embodiments, the slices 106 may be flush with one another.

Returning back to FIG. 7, in embodiments, the MRI controller 36 may be operative to acquire a baseline image (represented by T2 and arrow 110). As will be appreciated, the baseline image 110 may provide a reference point from which the diffusion of molecules (not shown) of interest, e.g., water, within the object may be measured from. While the diffusion gradient sequence 96 depicts the baseline image 110 as being acquired during TR 1, i.e., prior to applying the diffusion gradients 104 to the slices 106, it will be understood that the baseline image 110 may be acquired at other TRs, e.g., a TR occurring after the last TR during which diffusion gradients 104 are applied, or a TR occurring in-between TRs in which diffusion gradients 104 are applied. Further, while the baseline image 110 is depicted in FIG. 7 as a T2 weighted image, it will be understood that other imaging techniques may be utilized.

Figures 3, 4, 5:
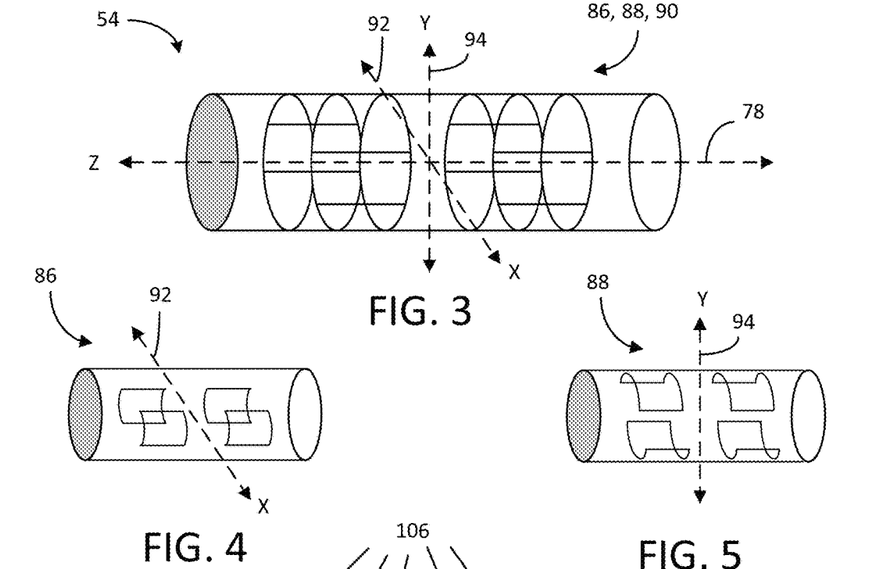
FIG. 3 is a diagram of a gradient coil assembly of the magnet assembly of FIG. 2, in accordance with an embodiment of the present invention.
FIG. 4 is a diagram of an x-axis gradient coil of the gradient coil assembly of FIG. 3, in accordance with an embodiment of the present invention.
FIG. 5 is a diagram of a y-axis gradient coil of the gradient coil assembly of FIG. 3, in accordance with an embodiment of the present invention.

Additionally, in embodiments, the number of TRs may correspond to the number of different diffusion gradients 104, e.g., the number of TRs may be equal to the number of differing diffusion gradients 104. For example, the diffusion gradient sequence 96 shown in FIG. 7 includes three (3) different diffusion gradients 104, e.g., x, y, and z, and therefore has three TRs, e.g., TRs 2-4, during which the diffusion gradients 104 are applied to the object 84. As stated above, however, the gradient coils 86, 88, and 90 may be used to generate/apply diffusion gradients 104 in directions that do not directly align with the x-axis 92 (FIGS. 3 and 4), y-axis 94 (FIGS. 3 and 5), and/or z-axis 78 (FIGS. 3 and 6). Accordingly, embodiments of the invention may have a diffusion gradient sequence 96 calling for two or more diffusion gradients 104, where each diffusion gradient 104 corresponds to a different direction, and where the diffusion gradient sequence 96 further calls for the same number of TRs as differing diffusion gradients 104, and/or directions, such that each of the different diffusion gradients 104 may be applied at least once to each slices 106 in the same cycling manner as described above.

Figure 11:
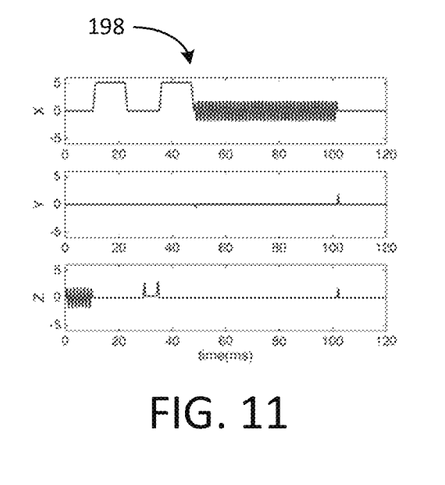
FIG. 11 is a diagram of a pulse sequence for applying a diffusion gradient for a slice of a TR for a tensor application, in accordance with an embodiment of the present invention.
Figure 12:
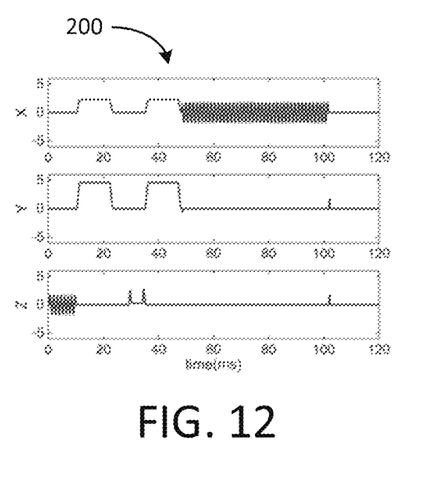
FIG. 12 is a diagram of a pulse sequence for applying a diffusion gradient for another slice of the TR for a tensor application, in accordance with an embodiment of the present invention.
Figure 13:
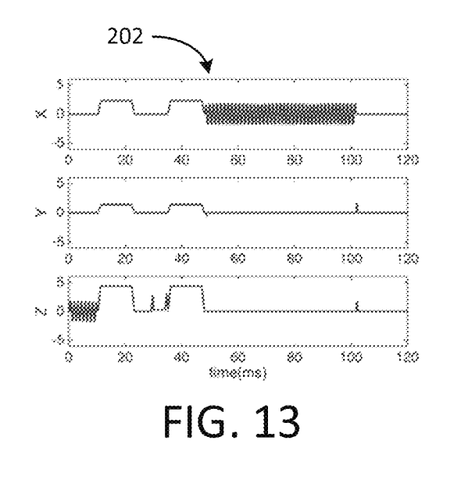
FIG. 13 is a diagram of a pulse sequence for applying a diffusion gradient for yet another slice of the TR for a tensor application, in accordance with an embodiment of the present invention.

As will also be appreciated, embodiments of the invention may be applied to Diffusion Tensor Imaging ("DTI") and may have x, y, and z diffusion gradients generated along pre-calculated tensor directions 198 (FIG. 11), 200 (FIG. 12), and 202 (FIG. 13), etc., respectively. For example, FIG. 11 depicts a pulse sequence for a diffusion gradient applied along the x-axis for a slice in a TR, FIG. 12 depicts a pulse sequence for a diffusion gradient applied in a direction having x, y, and z components of 0.446, 0.895, and 0.0, respectively for another slice in the TR, and FIG. 13 depicts a pulse sequence of a diffusion gradient applied in a direction having x, y, and z components of 0.447, 0.275, and 0.851, respectively for yet another slice in the TR. As such, some embodiments involving DTI may have gradients applied in six (6) directions.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a method for performing magnetic resonance diffusion weighted imaging of an object is provided. The method includes applying a plurality of diffusion gradients to a plurality of image slices of the object during a plurality of repetition times via an MRI system. A different diffusion gradient of the plurality is applied to each image slice during the same repetition time. In certain embodiments, the number of repetition times corresponds to the number of different diffusion gradients. In certain embodiments, each diffusion gradient of the plurality corresponds to a different direction. In certain embodiments, applying a plurality of diffusion gradients to a plurality of image slices of the object during a plurality of repetition times via an MRI system includes: applying a first diffusion gradient of the plurality in a first direction to a first image slice of the plurality during a first repetition time of the plurality; applying a second diffusion gradient in a second direction to a second image slice of the plurality during the first repetition time; applying the second diffusion gradient in the second direction to the first image slice during a second repetition time of the plurality; and applying the first diffusion gradient in the first direction to the second image slice during the second repetition time. In certain embodiments, the method further includes acquiring a baseline image of the object via the MRI system. In certain embodiments, the baseline image is acquired prior to applying the plurality of diffusion gradients to the plurality of image slices of the object during the plurality of repetition times. In certain embodiments, the baseline image is a T2 weighted image. In certain embodiments, the plurality of image slices is oriented along the same axis. In certain embodiments, the axis is a z-axis of a magnet assembly of the MRI system. In certain embodiments, the axis is a longitudinal axis of the object.

Other embodiments provide for an MRI system for performing magnetic resonance diffusion weighted imaging of an object. The MRI system includes an MRI controller in electronic communication with a magnet assembly. The MRI controller is operative to apply a plurality of diffusion gradients to a plurality of image slices of the object during a plurality of repetition times via the magnet assembly. A different diffusion gradient of the plurality is applied to each image slice during the same repetition time. In certain embodiments, the number of repetition times corresponds to the number of different diffusion gradients. In certain embodiments, each diffusion gradient of the plurality corresponds to a different direction. In certain embodiments, the MRI controller is further operative to: apply a first diffusion gradient of the plurality in a first direction to a first image slice of the plurality during a first repetition time of the plurality; apply a second diffusion gradient in a second direction to a second image slice of the plurality during the first repetition time; apply the second diffusion gradient in the second direction to the first image slice during a second repetition time of the plurality; and apply the first diffusion gradient in the first direction to the second image slice during the second repetition time. In certain embodiments, the MRI controller is further operative to acquire a baseline image of the object via the magnet assembly. In certain embodiments, the baseline image is acquired prior to applying the plurality of diffusion gradients to the plurality of image slices of the object during the plurality of repetition times. In certain embodiments, the baseline image is a T2 weighted image. In certain embodiments, the plurality of image slices is oriented along the same axis. In certain embodiments, the axis is a z-axis of a magnet assembly of the MRI system. In certain embodiments, the axis is a longitudinal axis of the object.

Yet still other embodiments provide for a non-transitory computer readable medium storing instructions. The stored instructions are configured to adapt an MRI controller to apply a plurality of diffusion gradients to a plurality of image slices of an object during a plurality of repetition times via a magnet assembly. A different diffusion gradient of the plurality is applied to each image slice during the same repetition time. In certain embodiments, the number of repetition times corresponds to the number of different diffusion gradients. In certain embodiments, each diffusion gradient of the plurality corresponds to a different direction. In certain embodiments, the stored instructions further adapt the MRI control to: apply a first diffusion gradient of the plurality in a first direction to a first image slice of the plurality during a first repetition time of the plurality; apply a second diffusion gradient in a second direction to a second image slice of the plurality during the first repetition time; apply the second diffusion gradient in the second direction to the first image slice during a second repetition time of the plurality; and apply the first diffusion gradient in the first direction to the second image slice during the second repetition time. In certain embodiments, the stored instructions further adapt the MRI control to acquire a baseline image of the object via the magnet assembly. In certain embodiments, the baseline image is acquired prior to applying the plurality of diffusion gradients to the plurality of image slices of the object during the plurality of repetition times. In certain embodiments, the baseline image is a T2 weighted image. In certain embodiments, the plurality of image slices is oriented along the same axis. In certain embodiments, the axis is a z-axis of a magnet assembly of the MRI system. In certain embodiments, the axis is a longitudinal axis of the object.

Accordingly, by alternating/cycling the diffusion gradients such that a different diffusion gradient is applied to each slice within a given TR, some embodiments of the invention significantly reduce the amount of stressor, e.g., the generation of heat, within the gradient coils, gradient amplifiers, and/or gradient power supplies of an encompassing MRI system. In other words, a y-gradient coil, amplifier, and/or corresponding power supply may be "rested" while an x-diffusion gradient is applied, and the x-gradient coil, amplifier, and/or corresponding power supply may be rested while the y-diffusion gradient is applied.

Further, some embodiments of the invention do not require periods of time, i.e., "dead time," between the generation/application of subsequent diffusion gradients in order to reduce the amount of heat generated within the gradient coils, gradient amplifiers, and/or corresponding power supplies. Accordingly, some embodiments of the invention provide for MRI system to have magnetically stronger gradient coils than those found in traditional MRI systems, while also allowing such MRI systems to achieve the same and/or faster scan times than traditional MRI systems. For example, some embodiments of the present invention provide for MRI systems capable of achieving clinically useful DWI at up to 70 mT/m.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A method for performing magnetic resonance diffusion weighted imaging of an object, the method comprising:
    applying a first radio frequency pulse to excite a first image slice during a first repetition time;
    applying a first pair of diffusion gradients in a first direction to the first image slice during the first repetition time;
    capturing the first image slice during the first repetition time by applying imaging gradients;
    applying a second radio frequency pulse to excite a second image slice during the first repetition time;
    applying a second pair of diffusion gradients in a second direction to the second image slice during the first repetition time after the first pair of diffusion gradients in the first direction to the first image slice have been applied, wherein the second direction is different from the first direction, and the second image slice is different from the first image slice; and capturing the second image slice during the first repetition time by applying the imaging gradients.

2. The method of claim 1, further comprising applying a third diffusion gradient in a third direction to a third image slice during the first repetition time, wherein the third direction is different from the first and second directions.

3. The method of claim 2, further comprising applying diffusion gradients during multiple repetition times, and the number of the repetition times corresponds to the number of different diffusion gradients.

4. The method of claim 3, further comprising:
applying the second pair of diffusion gradients in the second direction to the first image slice during a second repetition time;
applying the third diffusion gradient in the third direction to the second image slice during the second repetition time; and
applying the first pair of diffusion gradients in the first direction to the third image slice during the second repetition time.

5. The method of claim 1 further comprising:
acquiring a baseline image during a repetition time different from the first repetition time.

6. The method of claim 4, wherein the baseline image is a T2 weighted image.

7. The method of claim 1, wherein the plurality of image slices are oriented along the same axis.

8. The method of claim 7, wherein the axis is a longitudinal axis of the object.

9. An MRI system for performing magnetic resonance diffusion weighted imaging of an object, the MRI system comprising:
an MRI controller in electronic communication with a magnet assembly and configured to:
apply a first radio frequency pulse to excite a first image slice during a first repetition time;
apply a first pair of diffusion gradients in a first direction to the first image slice during a first repetition time;
capture the first image slice during the first repetition time by applying imaging gradients;
apply a second radio frequency pulse to excite a second image slice during the first repetition time;
apply a second pair of diffusion gradients in a second direction to the second image slice during the first repetition time after the first pair of diffusion gradients in the first direction to the first image slice have been applied, wherein the second direction is different from the first direction; and
capture the second image slice during the first repetition time by applying the imaging gradients.

10. The MRI system of claim 9, wherein the MRI controller is further configured to apply a third diffusion gradient in a third direction to a third image slice during the first repetition time, wherein the third direction is different from the first and second directions.

11. The MRI system of claim 10, wherein the MRI controller is further configured to apply diffusion gradients during multiple repetition times, and the number of the repetition times corresponds to the number of different diffusion gradients.

12. The MRI system of claim 11, wherein the MRI controller is further configured to:
apply the second pair of diffusion gradients in the second direction to the first image slice during a second repetition time;
apply the third diffusion gradient in the third direction to the second image slice during the second repetition time; and
apply the first pair of diffusion gradients in the first direction to the third image slice during the second repetition time.

13. The MRI system of claim 9, wherein the MRI controller is further configured to acquire a baseline image during a repetition time different from the first repetition time.

14. The MRI system of claim 9, wherein the plurality of image slices are oriented along a longitudinal axis of the object.

15. A non-transitory computer readable medium storing instructions, when executed by an MRI controller, causing the MRI controller to:
apply a first radio frequency pulse to excite a first image slice during a first repetition time;
apply a first pair of diffusion gradients in a first direction to the first image slice during a first repetition time;
capture the first image slice during the first repetition time by applying imaging gradients;
apply a second radio frequency pulse to excite a second image slice during the first repetition time;
apply a second pair of diffusion gradients in a second direction to the second image slice during the first repetition time after the first pair of diffusion gradients in the first direction to the first image slice have been applied, wherein the second direction is different from the first direction; and
capture the second image slice during the first repetition time by applying the imaging gradients.

16. The medium of claim 15, wherein the instructions further cause the MRI controller to
apply a third diffusion gradient in a third direction to a third image slice during the first repetition time, wherein the third direction is different from the first and second directions.

17. The medium of claim 16, wherein the instructions further cause the MRI controller to apply diffusion gradients during multiple repetition times, and the number of the repetition times corresponds to the number of different diffusion gradients.

18. The medium of claim 17, wherein the instructions further cause the MRI controller to:
apply the second pair of diffusion gradients in the second direction to the first image slice during a second repetition time;
apply the third diffusion gradient in the third direction to the second image slice during the second repetition time; and
apply the first pair of diffusion gradients in the first direction to the third image slice during the second repetition time.

19. The medium of claim 15, wherein the instructions further cause the MRI controller to acquire a baseline image during a repetition time different from the first repetition time.

20. The medium of claim 15, wherein the plurality of image slices are oriented along a longitudinal axis of the object.

* * * * *